United States Patent [19]

Tabone

[11] Patent Number: 5,740,708
[45] Date of Patent: Apr. 21, 1998

[54] SUCTION MICROTOME, PARTICULARLY FOR HISTOLOGICAL WORK AND THE LIKE

[75] Inventor: Hervé Tabone, Limonest, France

[73] Assignee: Microm Laborgeräte GmbH, Walldorf, Germany

[21] Appl. No.: 557,077

[22] PCT Filed: Jun. 2, 1994

[86] PCT No.: PCT/FR94/00648

§ 371 Date: Jan. 29, 1996

§ 102(e) Date: Jan. 29, 1996

[87] PCT Pub. No.: WO94/28390

PCT Pub. Date: Dec. 8, 1994

[30] Foreign Application Priority Data

Jun. 2, 1993 [FR] France .................. 93 06801

[51] Int. Cl.⁶ .................................................. B26D 7/18
[52] U.S. Cl. .................. 83/100; 83/171; 83/915.5
[58] Field of Search .................. 83/915.5, 100, 83/171, 165, 147, 167

[56] References Cited

U.S. PATENT DOCUMENTS

| | | |
|---|---|---|
| 2,901,944 | 9/1959 | Sparer ............................ 83/915.5 |
| 3,212,379 | 10/1965 | McCormick et al. ............ 83/915.5 |
| 3,649,108 | 3/1972 | Abrens et al. ................... 352/84 |
| 3,673,904 | 7/1972 | Cooper et al. ................... 83/171 |
| 3,832,923 | 9/1974 | Lassmann et al. ............... 83/16 |
| 4,184,472 | 1/1980 | Benedicto et al. ............... 125/23 R |
| 4,700,600 | 10/1987 | Pickett ............................ 83/915.5 |
| 4,752,347 | 6/1988 | Rada ............................... 156/382 |
| 5,255,585 | 10/1993 | Gordon .......................... 83/100 |

Primary Examiner—Maurina T. Rachuba

[57] ABSTRACT

A microtome includes a suction system that is integral with a knife carrier, which opposes the rolling up of tissue sections upon themselves and ensures evacuation of waste sections immediately after their appearance in the region of the sectioning blade of the knife carrier. The knife carrier has a suction cavity that is arranged in the immediate vicinity of the sectioning blade and is connected to a source of vacuum or reduced pressure. A cover is pivotably mounted on the body of the knife carrier. The cover has a u-shaped cross section, opened downwards, and profiled to cover the suction cavity and partially cover the sectioning blade. The cover defines a narrow free space in a form of a channel extending parallel to the upper face of the body of the knife carrier to guide a flow of suctioning air exerted on the sections. A valve has a closed position and an opened position for regulating the flow of suctioning air through the narrow free space.

9 Claims, 5 Drawing Sheets

FIG. 5
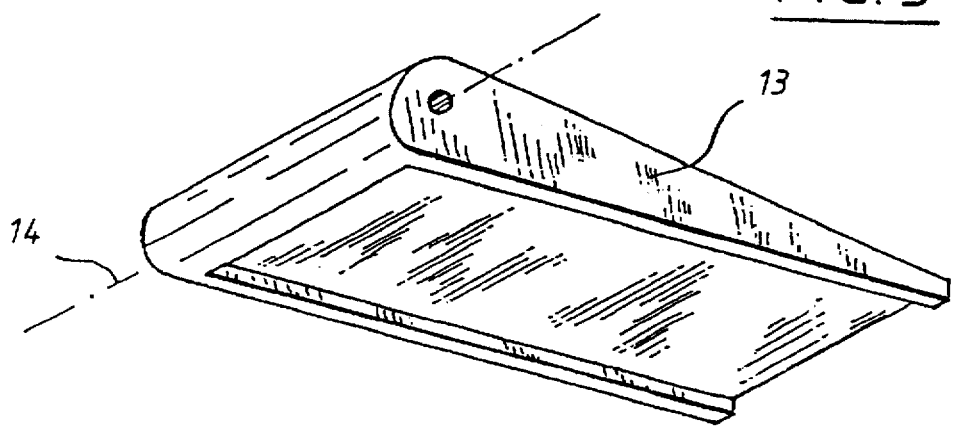
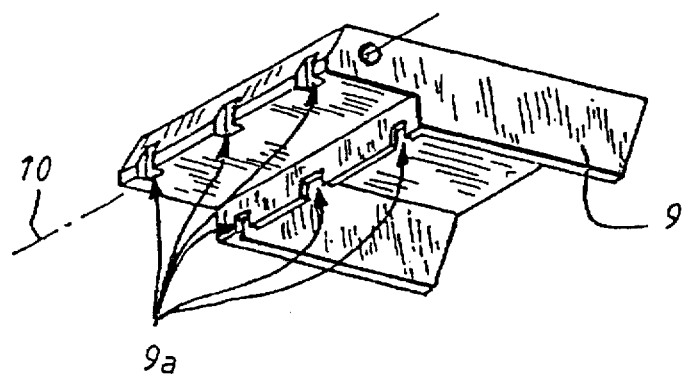
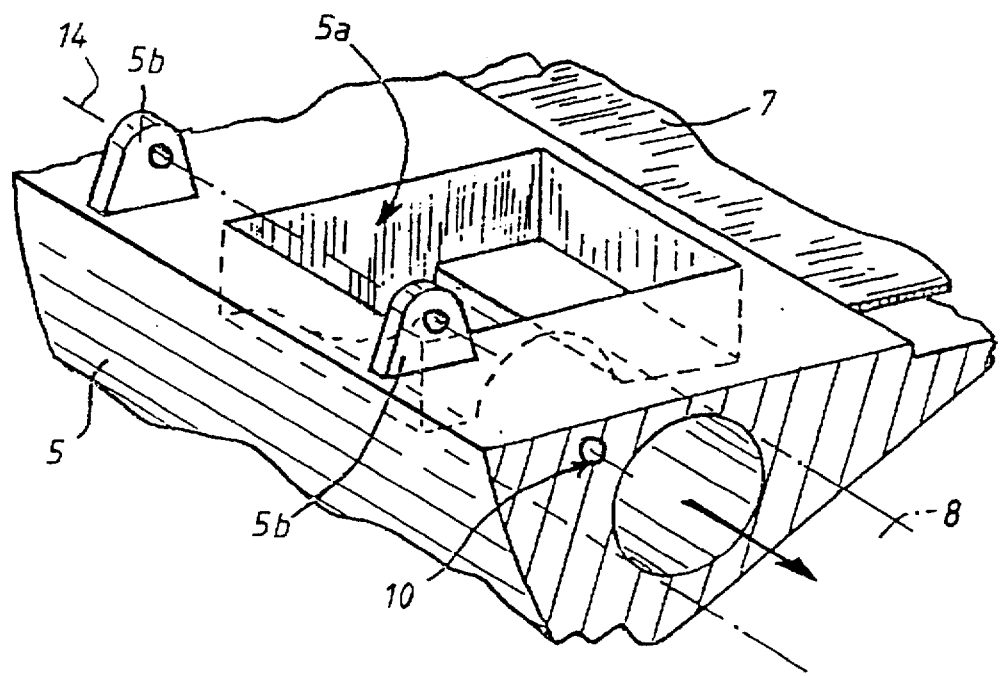

SUCTION MICROTOME, PARTICULARLY FOR HISTOLOGICAL WORK AND THE LIKE

BACKGROUND OF THE INVENTION

1. Field of the Invention

The present invention relates to a suction microtome, and more particularly, a suction microtome for histological work and the like.

2. Discussion of Prior Art

It is known that, for certain histological work, use is made of appliances known as "microtomes" which, working either at ambient temperature or in cryostatic enclosures, enable tissues to be sectioned into very fine slices, the thickness of cut being variable in practice from 0.5 to 60 microns.

The conventional microtomes generally have a support which is intended to receive the piece of tissue to be sectioned and which is actuated with an alternating movement combined with a micrometric advancing displacement oriented perpendicularly to the plane of the alternating movement. With this object carrier there is associated a knife carrier which is adjustable in orientation with respect to the support and is arranged to permit a blade to be mounted which is suitable for sectioning the piece of tissue integral with the alternating support.

The operations of sectioning are very delicate, and it can happen that the sections which are obtained roll up on themselves, leading to complications in picking them up. Moreover, waste, i.e., imperfect sections, are very frequent, and pollute the working space.

SUMMARY OF THE INVENTION

The present invention is intended more particularly to remedy these disadvantages, and consists in fact of endowing the microtome with a suction system which is integral with the knife carrier and which is arranged for selective control to favor flatness of the sections, by opposing their rolling up on themselves, or to ensure the evacuation of waste sections immediately after their appearance in the region of the cutting blade.

The microtome according to the invention includes: a tissue carrier support for receiving a piece of tissue from which the sections are to be cut and a knife carrier for interchangeably mounting a sectioning blade. The knife carrier has a body having an upper face at which the sectioning blade is mounted. The microtome also includes a mechanism suitable for providing an alternating movement between the tissue carrier support and the knife carrier combined with micrometric advancing movement between the tissue carrier support and the knife carrier perpendicular to the alternating movement. A suction cavity is formed in the upper face of the knife carrier. The suction cavity is connected to a source of vacuum or reduced pressure. A cover is pivotably mounted at the body of the knife carrier. The cover has a u-shaped cross-section, opened downwards, profiled to cover the suction cavity and to partially cover the sectioning blade and to define a narrow free space in a form of a channel extending parallel to the upper face of the body of the knife carrier for guiding a flow of suctioning air exerted on the sections between the cover and the upper face of the body of the knife carrier.

Advantageously, the microtome according to the invention also includes a valve for regulating the flow of suctioning air through the narrow free space, which valve has a closed position and an opened position. When the valve is closed, the narrow free space above the valve collects in a flat state the sections obtained.

BRIEF DESCRIPTION OF THE DRAWINGS

Preferred embodiments of the invention will now be described, taken together with the figures, in which:

The accompanying drawing, given by way of example, permits a better understanding of the invention, the characteristics which it exhibits, and the advantages which it is able to provide:

FIG. 5 shows, in perspective, in a separated state, the three elements which constitute the suction system of the microtome according to FIGS. 1–4.

DETAILED DESCRIPTION OF PREFERRED EMBODIMENTS

Figure 1:
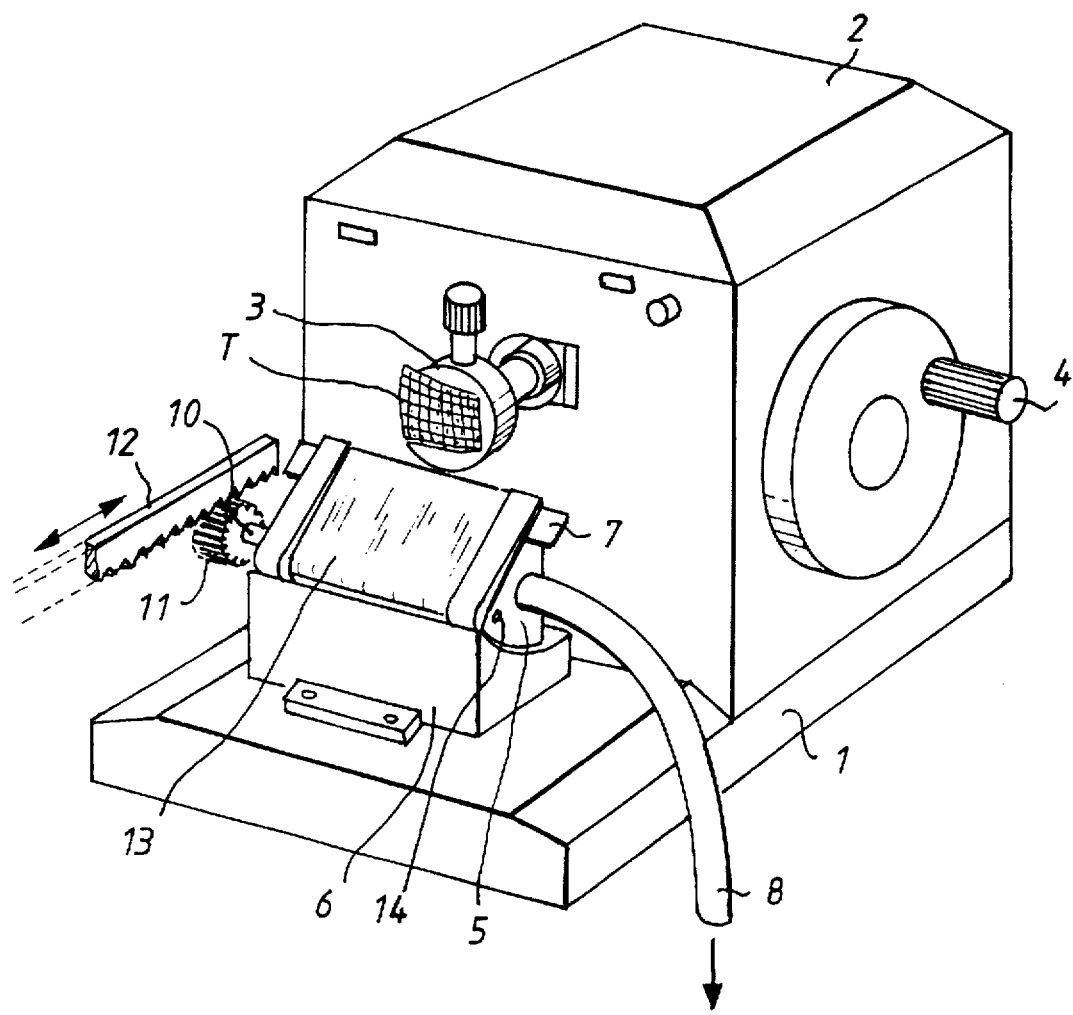
FIG. 1 is a perspective view showing a microtome set up according to the invention.

In a manner which is known per se, the microtome shown in FIG. 1 comprises a baseplate 1 on which is fixed a housing 2 enclosing the usual mechanism actuated to impart to a front support 3 an alternating vertical displacement combined with a micrometric horizontal advance, which mechanism is operated by a lateral handle 4 in the case considered. The portion of the baseplate 1 which is disposed forward of the housing 2 receives the body 5 of a knife carrier which is fixed on a base 6 so as to be adjustable in inclination.

As shown in FIGS. 2–5, the face of the body 5 is turned obliquely upwards to effect the interchangeable mounting of a blade 7 whose cutting edge slightly projects beyond the said face, in order to be able to come into contact with the piece of tissue T which is fixed on the support 3 for the operation of sectioning.

According to the invention, this upper face is hollowed out into a cavity 5a which extends laterally to permit connection of a flexible conduit 8, which ends in a source of vacuum or of reduced pressure whose rate of flow is advantageously capable of being regulated by the user, for example by means of a control valve (not shown). The upper opening of the cavity 5a is disposed immediately below the lower edge of the blade 7 and in this opening the lateral wings of the rocking flap valve 9, having a U-shaped cross-section and being disposed in the extension of the blade 7, are attached.

The angular movement of the flap valve 9 can be effected in any appropriate manner. Use can be made of a cam system, but in the embodiment example considered, it has been supposed that this flap valve 9 is integral with a shaft 10 having a pinion 11 keyed to one of its extended ends and actuated by a rack 12.

It should be observed here that the flap valve 9 does not effect a perfect obturation of the opening of the cavity 5a. The heel of this flap valve which is disposed behind the shaft 10, and also the lower edge of a partition provided in front of the said shaft, are both cut away by notches 9a which permit the passage of a small flow of air. The suction effect thus produced is exerted on the sections produced by the blade 7, preventing the sections rolling up on themselves.

This advantageous result can be further improved by means of a retractable cover 13 having a U-shaped cross section, open downwards, so as to cover the flap valve 9. This cover 13 is mounted to be able to be eclipsed at the right moment, for example by being mounted on a pivot 14 supported by lugs 5b of the body 5. It will be seen that the free edge of this cover 13 is located beyond the free edge of the flap valve 9 so as to partially cover the blade 7.

Figure 2:
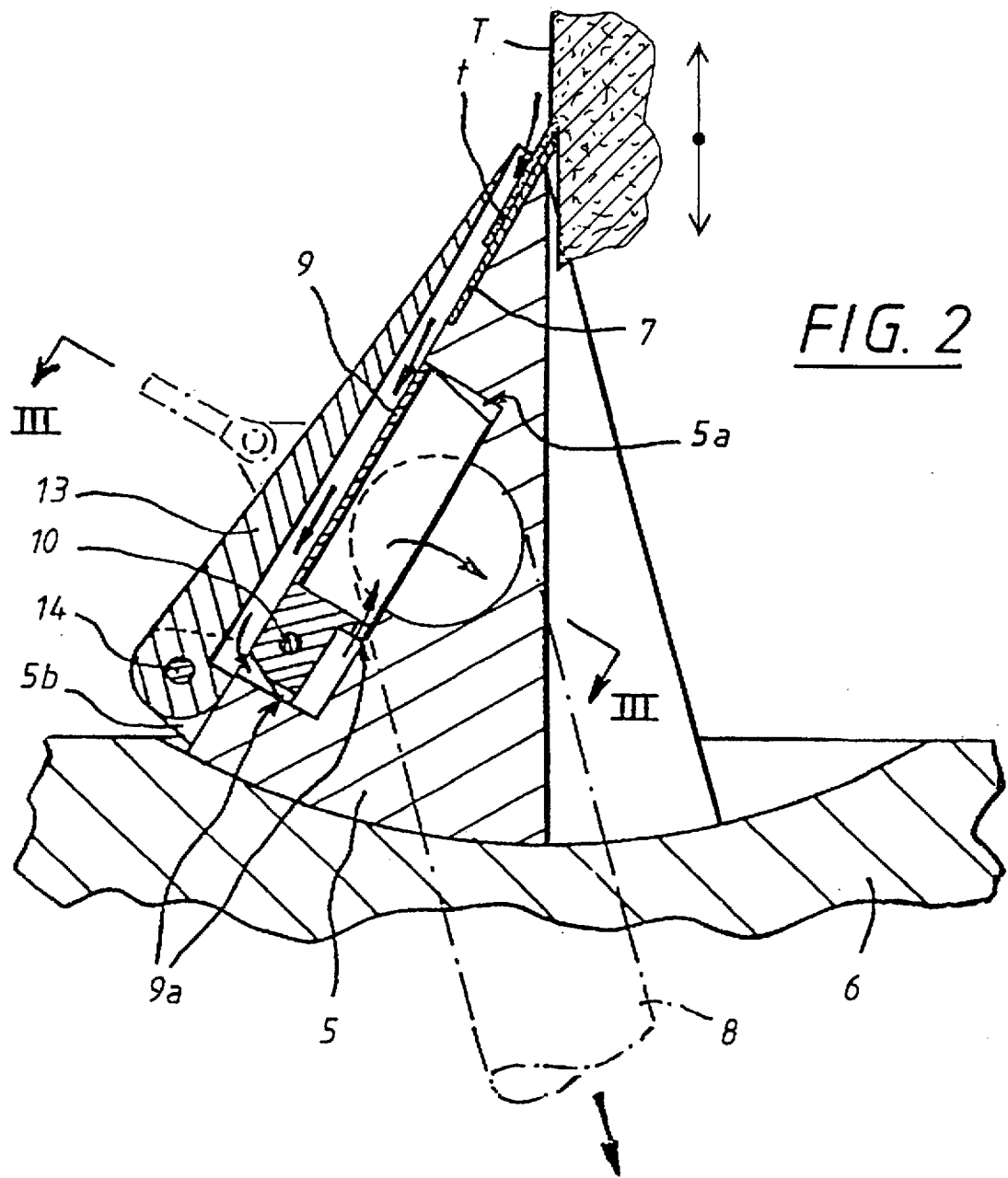
FIG. 2 is a transverse section through the knife carrier of the microtome according to FIG. 1.
Figure 3:
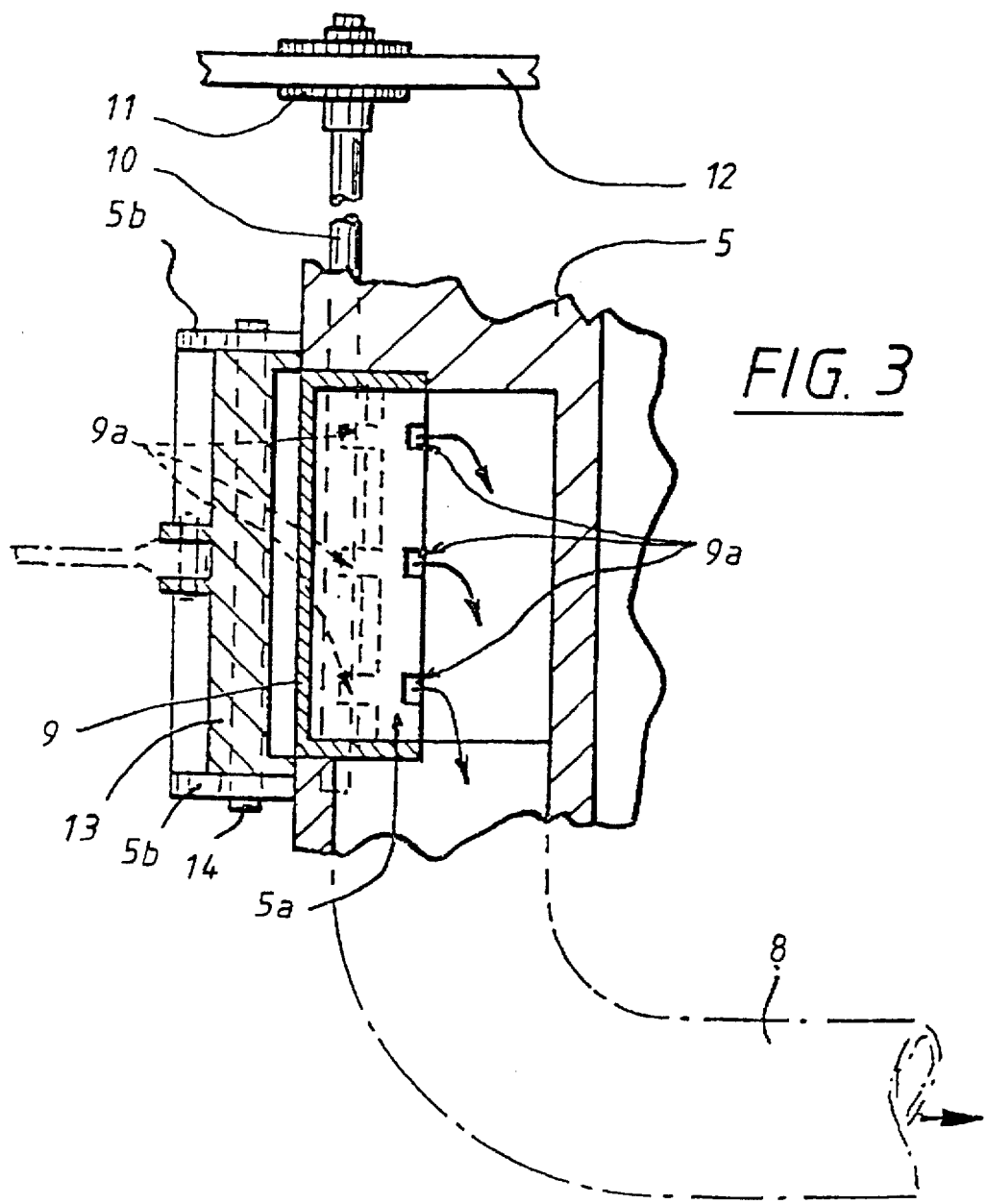
FIG. 3 is a section, on a greater scale, along the plane shown by III—III in FIG. 2.
Figure 4:
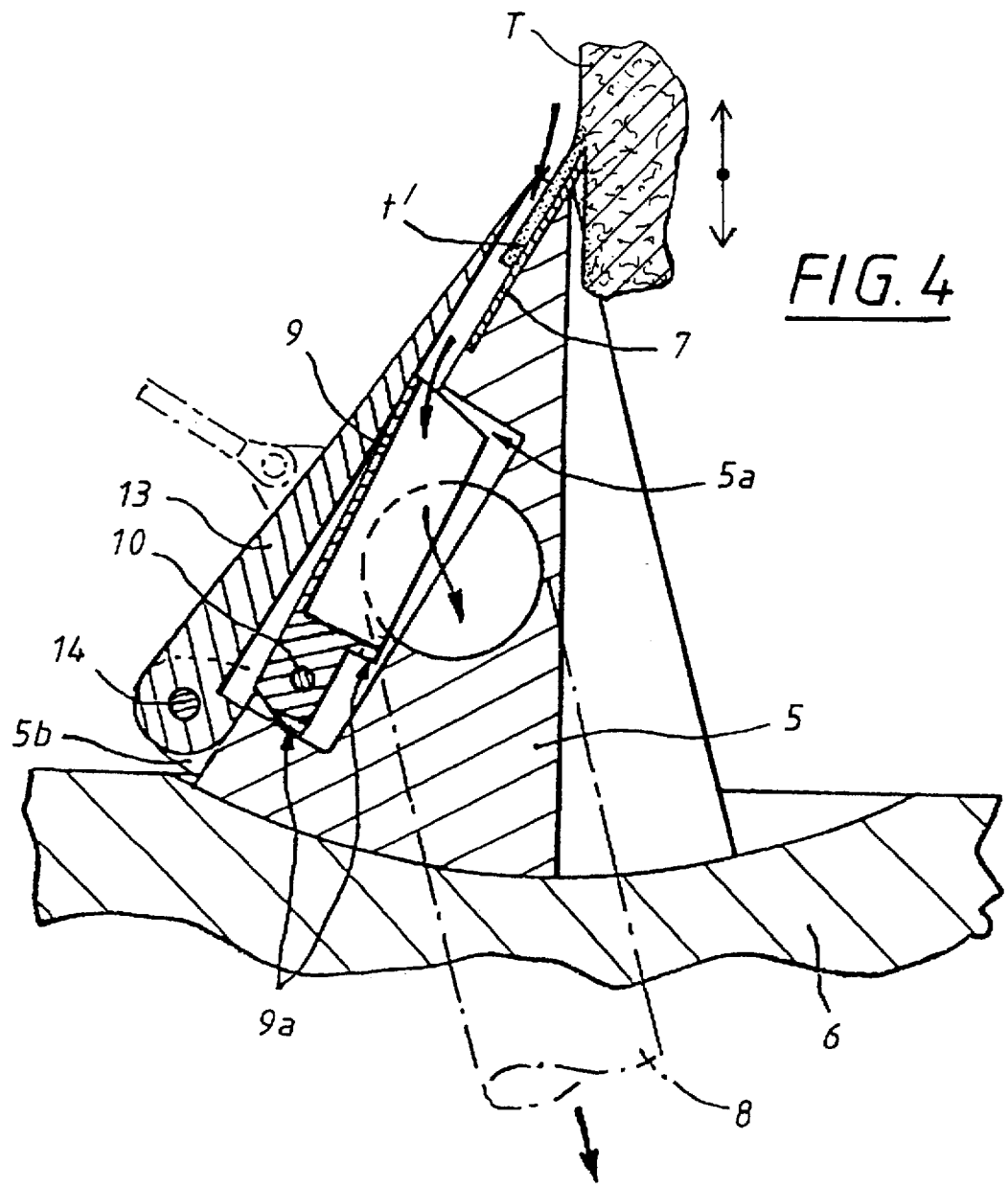
FIG. 4 reproduces FIG. 2 in the open position of the flap valve.

During the use of the microtome, the flap valve 9 is normally kept in the closed position as shown in FIG. 2. The slice or section t detached by the blade 7 from the object T to be sectioned slides along this blade, this displacement being facilitated by the suction flow which is permitted by the notches 9a and which flows in the narrow free space formed between the flap valve 9 and the cover 13. This suction radically prevents the rolling up on itself of the section t, which can be finally collected in a flat state by means of the momentary retraction of the cover 13 by tilting around its pivot 14.

If on the other hand the section t (FIG. 4) detached by blade 7 from the object T is not suitable and should, in the operator's opinion, be considered as an unusable reject, the said operator actuates the flap valve 9 to open, so that the strongly reduced pressure which exists in the cavity 5a ensures the aspiration of this section t, which is immediately removed through the duct 8, the latter possibly being equipped with a filter to facilitate the collection of waste materials thus taken out of the working chamber of the cryostat which encloses the microtome.

In this manner, the accumulation of waste in the working chamber is avoided; this clearly facilitates the process of cleaning and decontamination of the said chamber.

It should furthermore be understood that the preceding description has been given only by way of example and in no way limits the field of the invention, which is not departed from on replacing the described details of execution with any other equivalent details. It is particularly intended that the invention be applicable in the case in which the motor mechanism is associated with the knife carrier in order to impart to the latter an alternating movement and a micrometric advance with respect to a fixed tissue carrier.

I claim:

1. A microtome for cutting sections from a piece of tissue, comprising:

a tissue carrier support for receiving said piece of tissue from which said sections are to be cut, a knife carrier for interchangeably mounting a sectioning blade, said knife carrier having a body and said body having an upper face at which said sectioning blade is mounted, a mechanism suitable for providing an alternating movement between said tissue carrier support and said knife carrier combined with micrometric advancing movement between said tissue carrier support and said knife carrier perpendicular to said alternating movement, a suction cavity formed in said upper face of said knife carrier, said suction cavity being connected to a source of vacuum or reduced pressure, and a cover pivotably mounted at said body of said knife carrier, which cover can be pivoted to lie on said upper face of said body of said knife carrier, said cover being profiled to cover said suction cavity and having a length also to partially cover said sectioning blade when covering said suction cavity, said cover having a u-shaped cross-section, opened downwards, whereby a narrow free space in form of a channel extending parallel to said upper face of said body of said knife carrier is provided between said upper face of said body of said knife carrier and said cover when said cover is pivoted to lie on said upper face of said body of said knife carrier, and whereby, when operating said source of vaccuum or reduced pressure, a flow of suctioning air exerted on said sections is provided through said narrow free space.

2. A microtome for cutting sections from a piece of tissue, comprising:

a tissue carrier support for receiving said piece of tissue from which said sections are to be cut, a knife carrier for interchangeably mounting a sectioning blade, said knife carrier having a body and said body having an upper face at which said sectioning blade is mounted, a mechanism suitable for providing an alternating movement between said tissue carrier support and said knife carrier combined with micrometric advancing movement between said tissue carrier support and said knife carrier perpendicular to said alternating movement, a suction cavity formed in said upper face of said knife carrier, said suction cavity being connected to a source of vacuum or reduced pressure, a cover pivotably mounted at said body of said knife carrier, which cover can be pivoted to lie on said upper face of said body of said knife carrier, said cover being profiled to cover said suction cavity and having a length also to partially cover said sectioning blade when covering said suction cavity, said cover having a u-shaped cross-section opened downwards, whereby a narrow free space in form of a channel extending parallel to said upper face of said body of said knife carrier is provided between said upper face of said body of said knife carrier and said cover when said cover is pivoted to lie on said upper face of said body of said knife carrier, and whereby when operating said source of vaccuum or reduced pressure a flow of suctioning air exerted on said sections is provided through said narrow free space, and a valve having a closed position and an opened position for regulating said flow of suctioning air through said narrow free space.

3. The microtome according to claim 2, wherein in said closed position of said valve a small flow of air is exerted on said sections, and in said opened position of said valve a strong flow of air is exerted on said sections adequate to ensure aspiration of said sections into said suction cavity.

4. A microtome for cutting sections from a piece of tissue, comprising:

a tissue carrier support for receiving said piece of tissue from which said sections are to be cut, a knife carrier for interchangeably mounting a sectioning blade, said knife carrier having a body and said body having an upper face at which said sectioning blade is mounted, a mechanism suitable for providing an alternating movement between said tissue carrier support and said knife carrier combined with micrometric advancing movement between said tissue carrier support and said knife carrier perpendicular to said alternating movement, a suction cavity formed in said upper face of said knife carrier, a cover pivotable mounted at said body of said knife carrier, said cover having a u-shaped cross-section, opened downwards, profiled to cover said suction, cavity and to partially cover said sectioning blade and to define a narrow free space in a form of a channel extending parallel to said upper face of said body of said knife carrier for guiding a flow of suctioning air exerted on said sections between said cover and said upper face of said body of said knife carrier.

5. The microtome according to claim 4, wherein said cover has sides at which said cover is mounted at said body of said knife holder, and said narrow free space between said cover and said body of said knife holder is closed at said sides of said cover.

6. The microtome according to claim 4, wherein said cover has a first end and a second end opposite said first end, said first end of said cover partially covering said sectioning blade, said cover being mounted at said second end at said knife carrier, and wherein said narrow free space between said cover and said body of said knife holder is closed at said second end of said cover.

7. A microtome for cutting sections from a piece of tissue, comprising:

a tissue carrier support for receiving said piece of tissue from which said sections are to be cut, a knife carrier for interchangeably mounting a sectioning blade, said knife carrier having a body and said body having an upper face at which said sectioning blade is mounted, a mechanism suitable for providing an alternating movement between said tissue carrier support and said knife carrier combined with micrometric advancing movement between said tissue carrier support and said knife carrier perpendicular to said alternating movement, a suction cavity formed in said upper face of said knife carrier, said suction cavity being connected to a source of vaccuum or reduced pressure, and a cover pivotably mounted at said body of said knife carrier, said cover having a u-shaped cross-section, opened downwards, profiled to cover said suction cavity and to partially cover said sectioning blade and to define a narrow free space in a form of a channel extending parallel to said upper face of said body of said knife carrier for guiding a flow of suctioning air exerted on said sections between said cover and said upper face of said body of said knife carrier, wherein said narrow free space communicates with said suction cavity.

8. The microtome according to claim 7, wherein said cover has sides at which said cover is mounted at said body of said knife holder, and said narrow free space between said cover and siad body of said knife holder is closed at said sides of said cover.

9. The microtome according to claim 7, wherein said cover has a first end and a second end opposite said first end, said first end of said cover partially covering said sectioning blade, said cover being mounted at said second end at said knife carrier, and wherein said narrow free space between said cover and said body of said knife holder is closed at said second end of said cover.

* * * * *